United States Patent
Matvienko et al.

(10) Patent No.: US 7,485,707 B2
(45) Date of Patent: Feb. 3, 2009

(54) THERMALLY STABLE CRYSTALLINE EPIRUBICIN HYDROCHLORIDE AND METHOD OF MAKING THE SAME

(75) Inventors: Victor Matvienko, Donetsk (UA); Alexey Matvyeyev, Donetsk (UA); Alexander F. Zabudkin, Donetsk (UA); Aleksandr M. Itkin, San Diego, CA (US)

(73) Assignee: Solux Corporation, San Diego, CA (US)

( * ) Notice: Subject to any disclaimer, the term of this patent is extended or adjusted under 35 U.S.C. 154(b) by 206 days.

(21) Appl. No.: 10/877,221

(22) Filed: Jun. 25, 2004

(65) Prior Publication Data

US 2006/0063726 A1    Mar. 23, 2006

Related U.S. Application Data

(60) Provisional application No. 60/484,132, filed on Jul. 2, 2003.

(51) Int. Cl.
*C07H 15/24* (2006.01)
(52) U.S. Cl. ....................................................... 536/6.4
(58) Field of Classification Search ................. 536/6.4; 514/34

See application file for complete search history.

(56) References Cited

U.S. PATENT DOCUMENTS

| | | | |
|---|---|---|---|
| 4,112,076 A | | 9/1978 | Arcamone |
| 4,345,068 A | | 8/1982 | Suarato |
| 4,861,870 A | | 8/1989 | Oppico |
| 5,091,373 A | * | 2/1992 | Gatti et al. .................... 514/34 |
| 5,874,550 A | * | 2/1999 | van der Rijst et al. ......... 536/6.4 |
| 5,945,518 A | | 8/1999 | Bigatti |
| 6,087,340 A | | 7/2000 | Gatti |
| 6,376,469 B1 | * | 4/2002 | Shimago et al. ............... 514/34 |

OTHER PUBLICATIONS

PCT International Search Report for PCT/US2004/020679, Applicant Solux Corporation, Form PCT/ISA/210 and 220, dated May 4, 2006 (5 pages).
PCT Written Opinion for PCT/US2004/020679, Applicant Solux Corporation, Form PCT/ISA/237, dated May 4, 2006 (4 pages).

* cited by examiner

*Primary Examiner*—Elli Peselev
(74) *Attorney, Agent, or Firm*—Vista IP Law Group LLP

(57) ABSTRACT

A crystalline form of epirubicin hydrochloride, named herein as "type II" crystalline epirubicin hydrochloride, has excellent thermal stability. Type II crystalline epirubicin hydrochloride has a powder X-ray diffraction pattern having average values of diffraction angle ($2\theta$) and relative intensity P(%) as presented in the following table:

| Diffraction Angle $2\Theta$ | Relative Intensity P (%) |
|---|---|
| 5.236 | 9.8 |
| 9.212 | 12.5 |
| 13.732 | 15.5 |
| 16.446 | 4.8 |
| 18.234 | 5 |
| 21.114 | 9.7 |
| 22.529 | 25.5 |
| 24.071 | 29.9 |
| 25.879 | 18.4 |
| 27.762 | 16.5 |
| 29.757 | 10.1 |
| 34.392 | 4.4 |
| 38.157 | 13.1 |
| 44.293 | 5.9 |
| 64.699 | 7.7 |
| 77.815 | 100. |

8 Claims, 7 Drawing Sheets

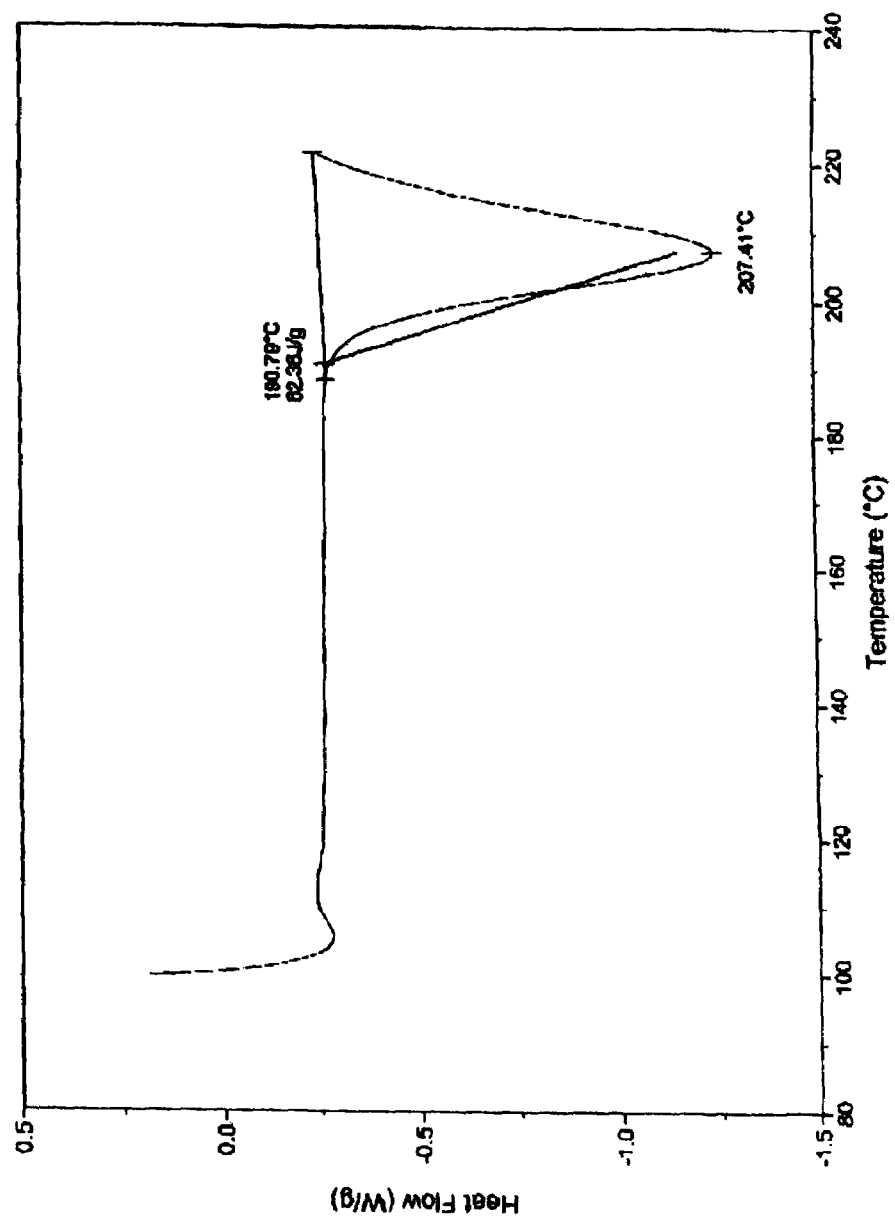
FIG. 1. Thermal analysis of crystalline epirubicin hydrochloride type II.

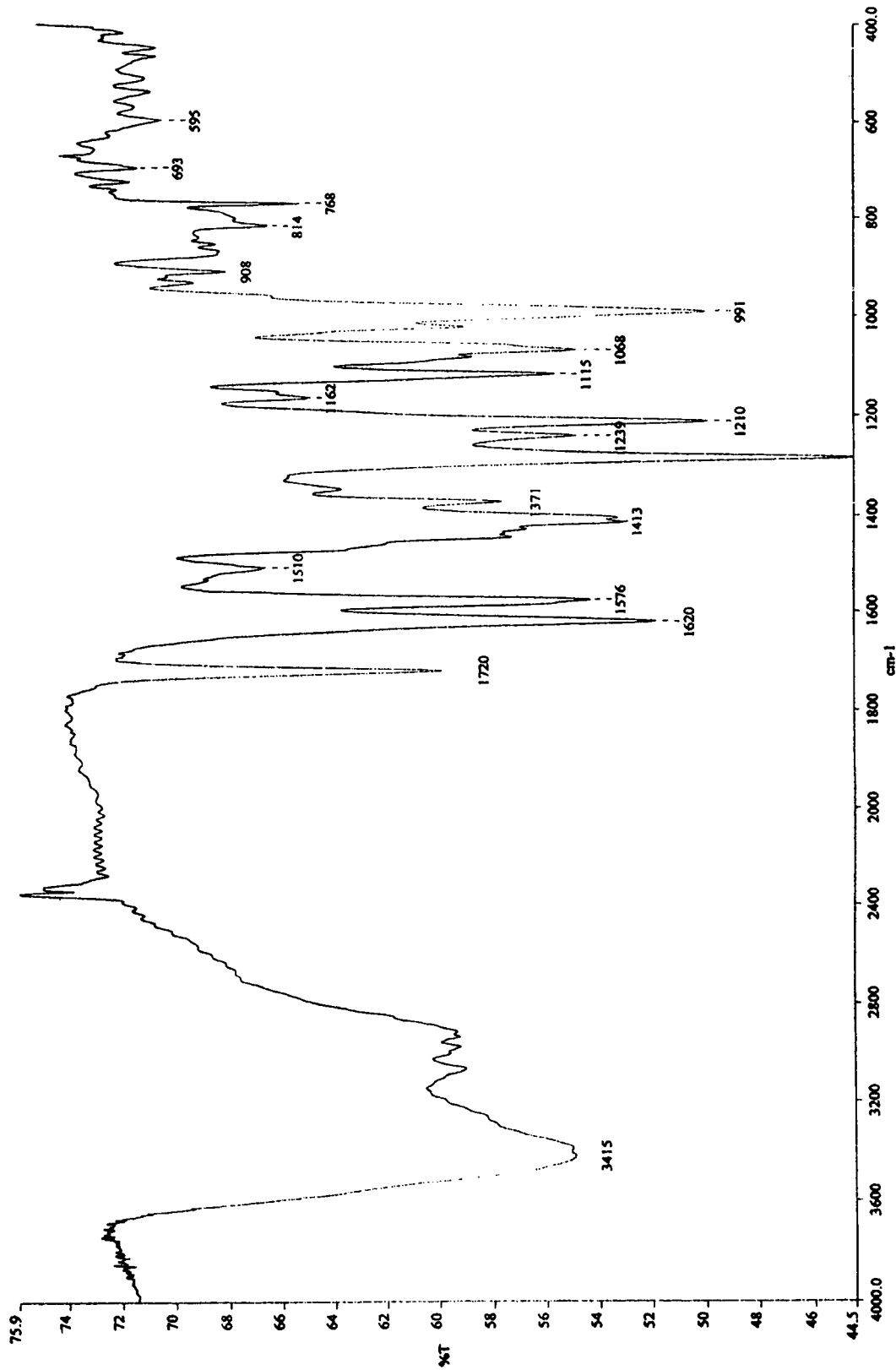
FIG. 2. IR-Spectrum of crystalline epirubicin hydrochloride type II.

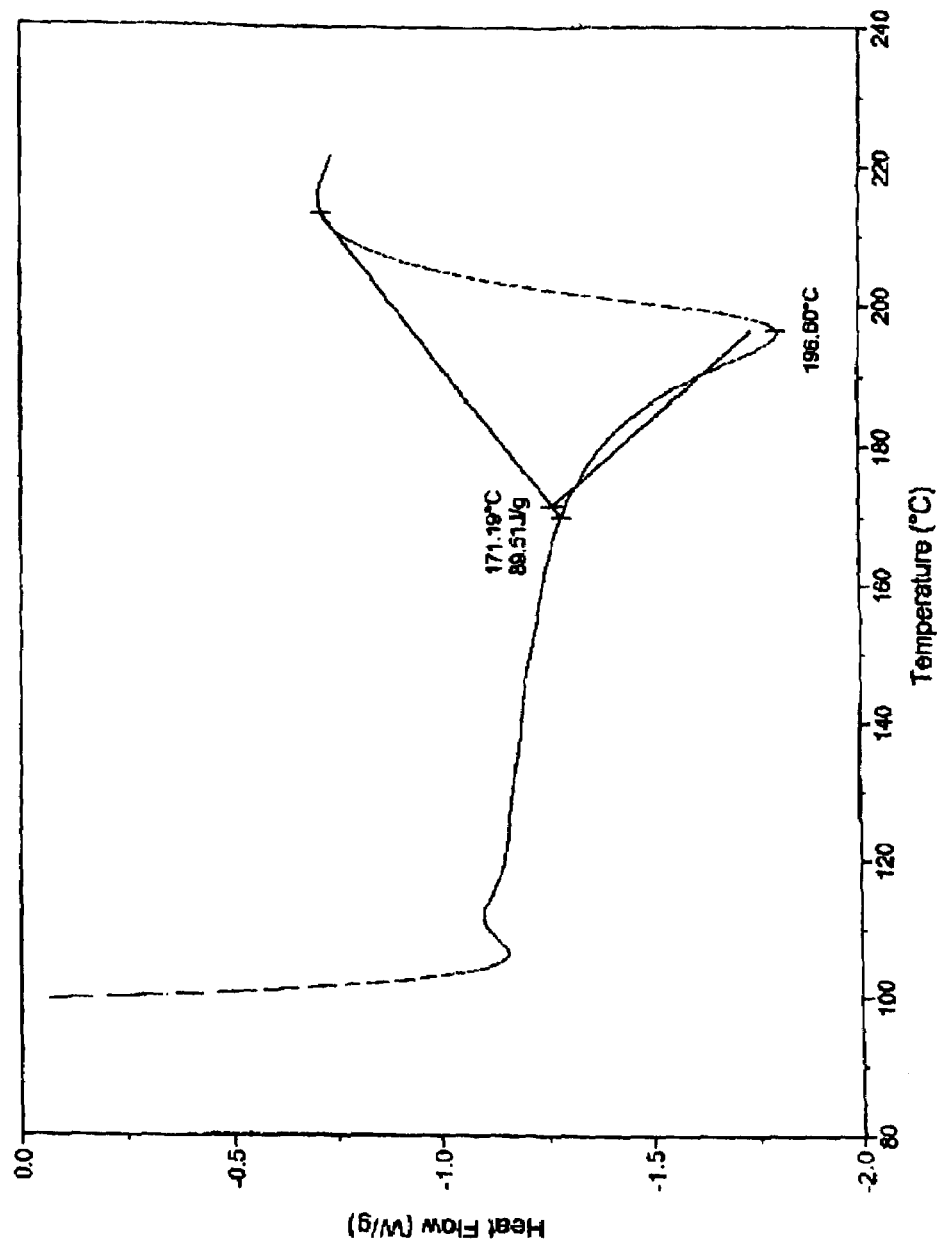
FIG. 3. Thermal analysis of crystalline epirubicin hydrochloride type I.

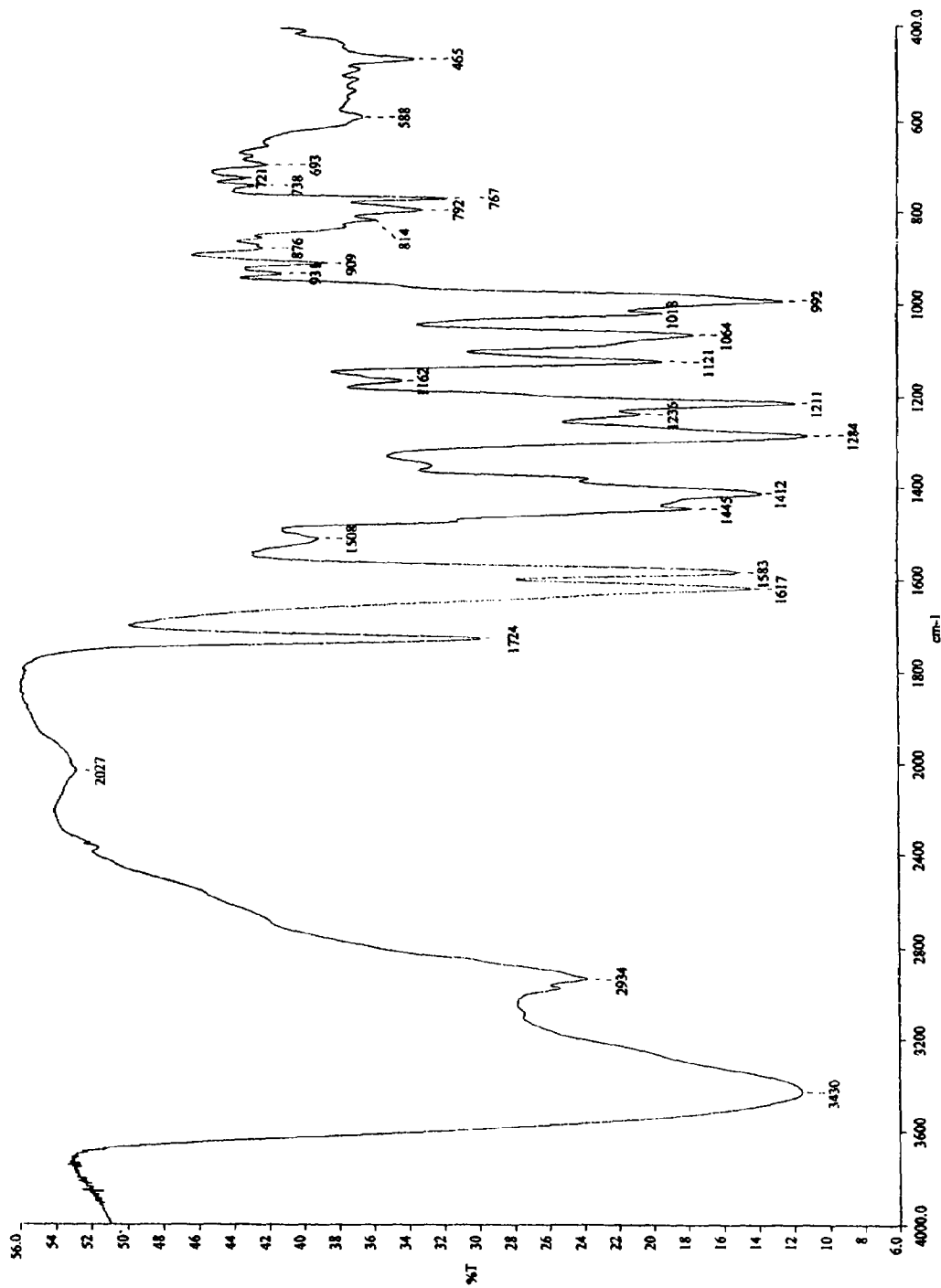
FIG. 4. IR-Spectrum of crystalline epirubicin hydrochloride type I.

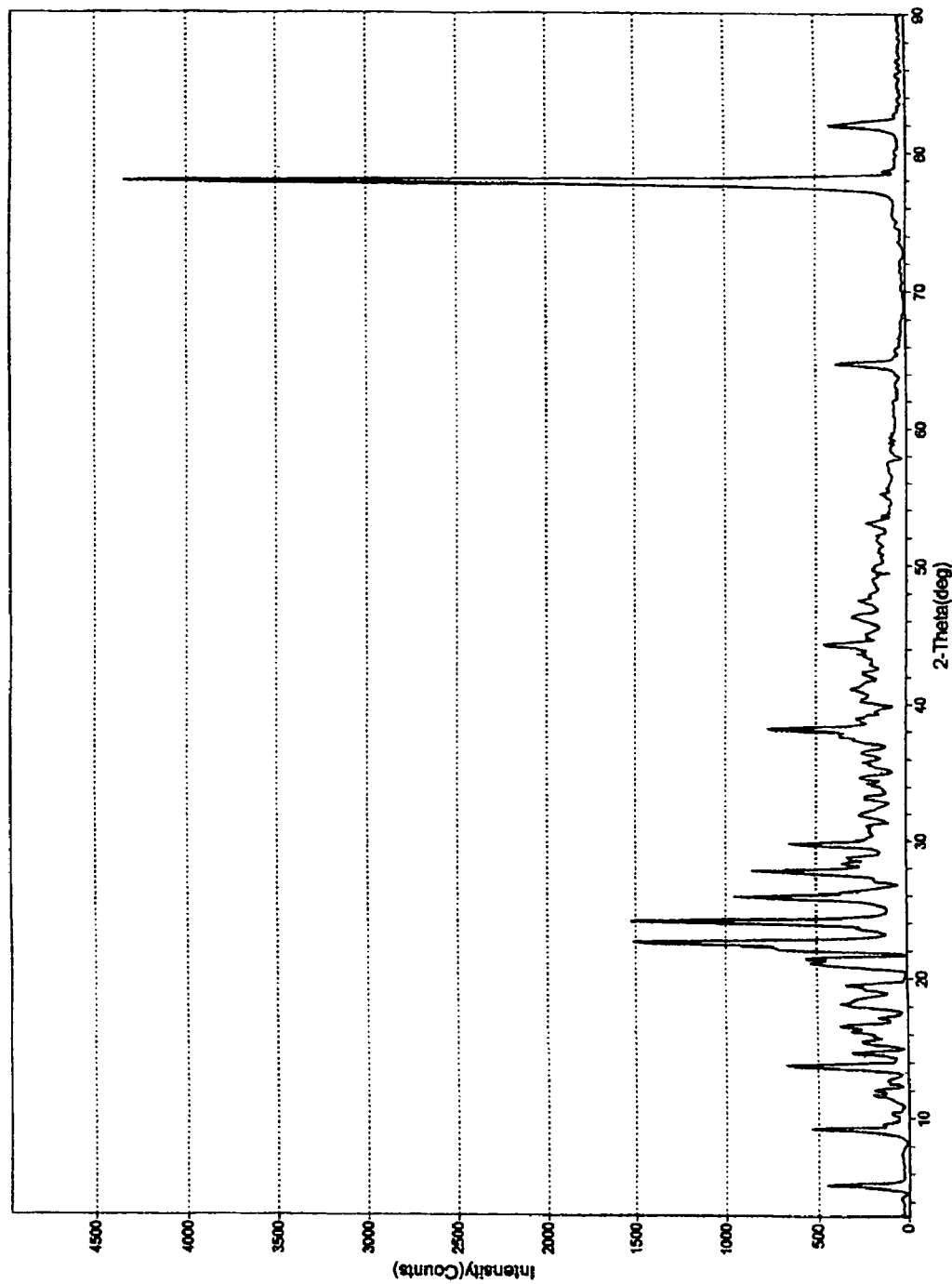
FIG. 5. Powder x-ray diffraction spectrum of crystalline epirubicin hydrochloride type II.

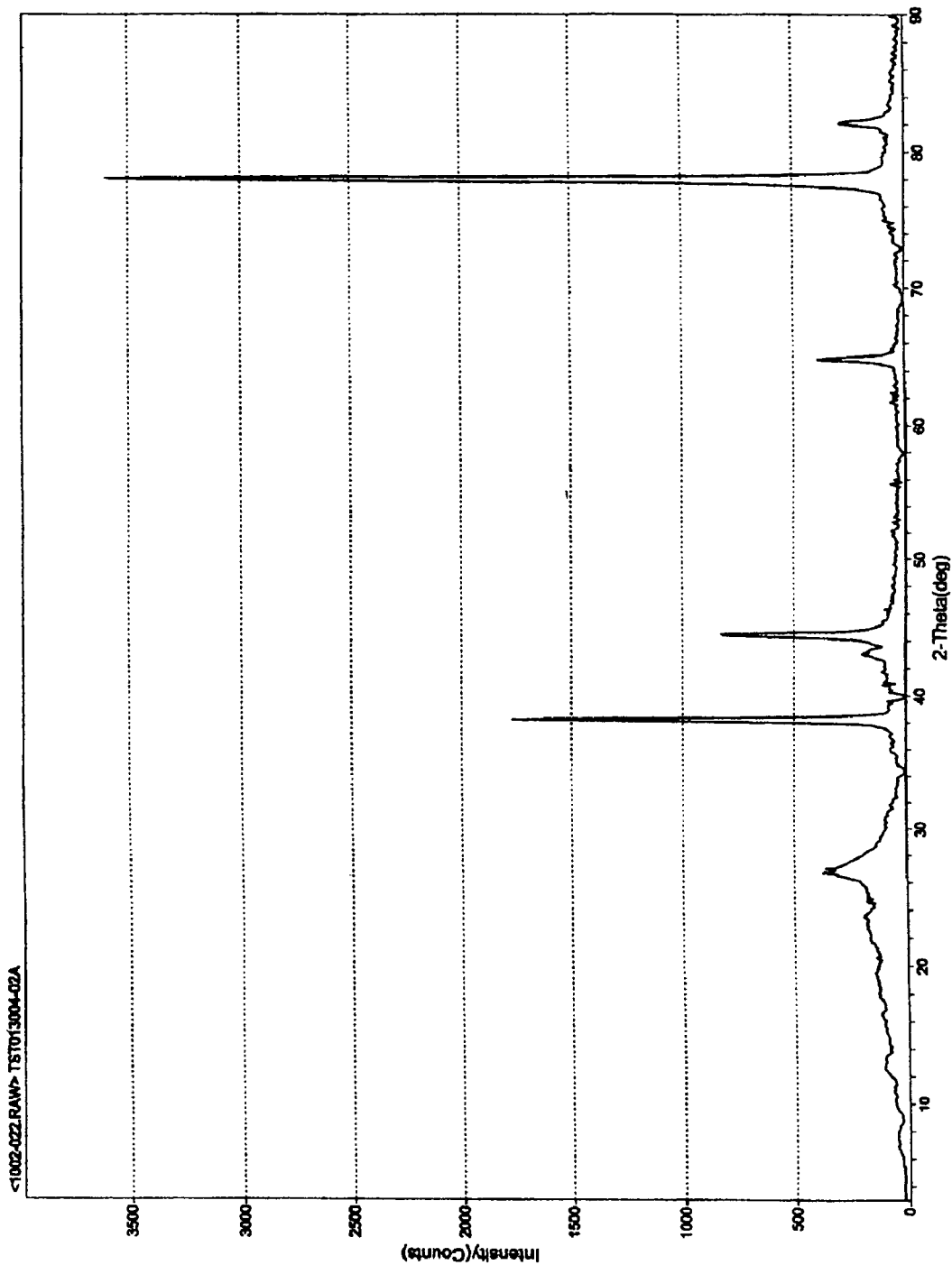
FIG. 6. Powder x-ray diffraction spectrum of crystalline epirubicin hydrochloride type I.

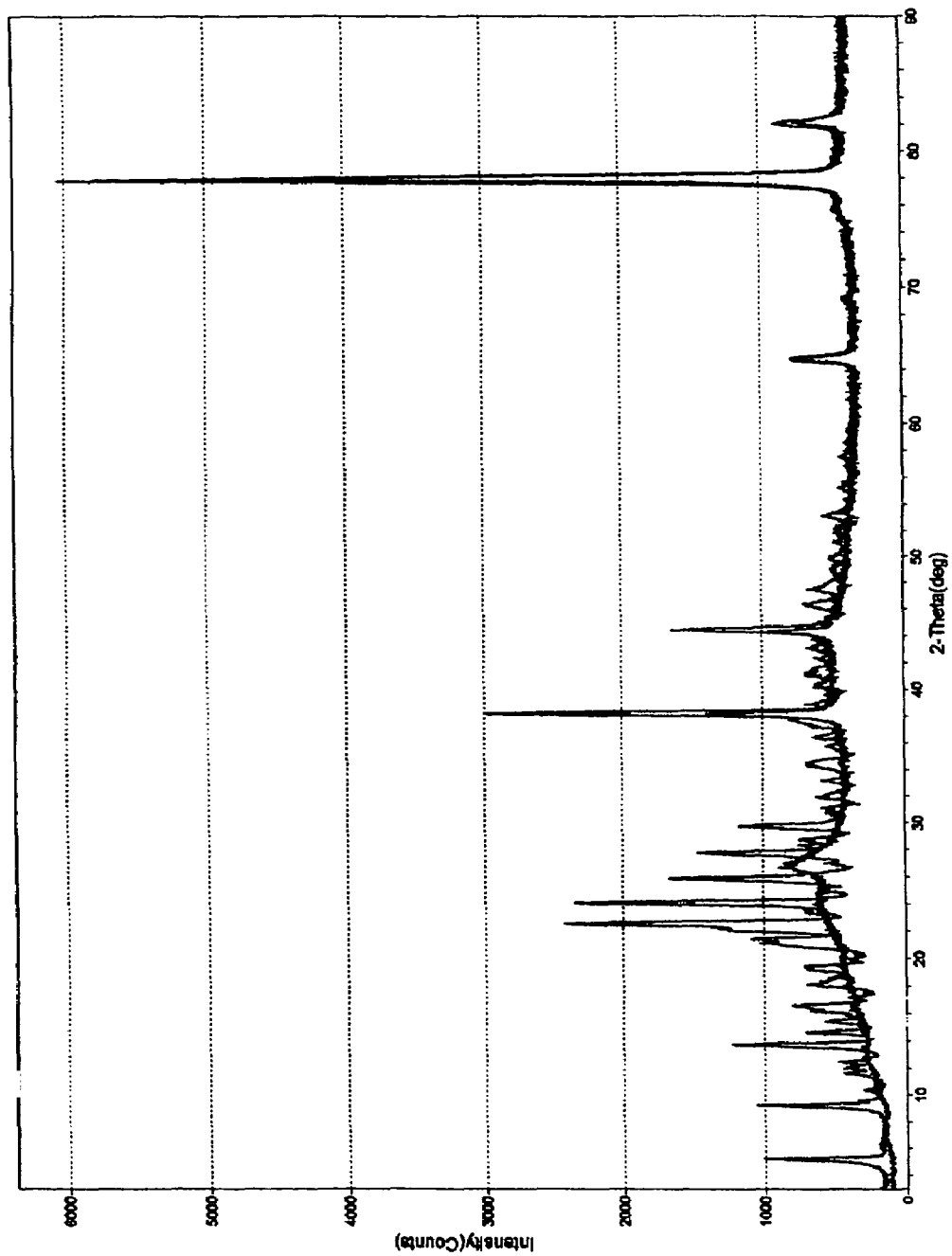
FIG. 7. Powder x-ray diffraction spectrum of crystalline epirubicin hydrochloride type I and type II.

THERMALLY STABLE CRYSTALLINE EPIRUBICIN HYDROCHLORIDE AND METHOD OF MAKING THE SAME

RELATED APPLICATIONS

This Application claims the benefit of U.S. provisional Application No. 60/484,132 filed on Jul. 2, 2003. U.S. provisional Application No. 60/484,132 is incorporated by reference as if set forth fully herein.

FIELD OF THE INVENTION

The field of the invention generally relates to crystalline forms of epirubicin hydrochloride, a compound which is useful as an anticancer chemotherapeutic drug. In particular, the field of the invention relates to a particular crystalline form of epirubicin hydrochloride which is distinguished by its improved thermal stability. In addition, the invention relates to methods of manufacturing the aforementioned crystalline form of epirubicin hydrochloride as well as to methods of using the aforementioned crystalline form of epirubicin hydrochloride to treat human and/or animal cancers.

BACKGROUND OF THE INVENTION

Anthracyclines form one of the largest families of naturally occurring bioactive compounds. Several members of this family have shown to be clinically effective anti-neoplastic agents. These include, for example, daunorubicin, doxorubicin, idarubicin, epirubicin, pirarubicin, zorubicin, aclarubicin, and carminomycin. For instance, these compounds have shown to be useful in bone marrow transplants, stem cell transplantation, treatment of breast carcinoma, acute lymphocytic and non-lymphocytic leukemia, chronic lymphocytic leukemia, non-Hodgkin's lymphoma, and other solid cancerous tumors.

U.S. Pat. Nos. 4,112,076, 4,345,068, 4,861,870, 5,945, 518, and 5,874,550 disclose the preparation of epirubicin hydrochloride and its usage as an anticancer agent, which is represented by the formula:

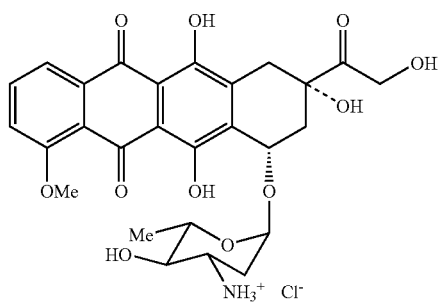

Currently, there are two major methods of extraction of epirubicin hydrochloride from solutions. The first method involves the treatment of the organic solution of epirubicin base with a solution of hydrogen chloride in methanol. See e.g., U.S. Pat. No. 4,112,076. Alternatively, the second method involves the precipitation of epirubicin hydrochloride from an aqueous or organo-aqueous solution with the aid of acetone. See e.g., U.S. Pat. No. 4,861,870.

U.S. Pat. No. 6,087,340 discloses an injectable ready-to-use solution containing epirubicin hydrochloride. More specifically, the '340 patent discloses a stable, injectable, sterile, pyrogen-free, anthracycline glycoside solution which consists essentially of a physiologically acceptable salt of an anthracycline glycoside dissolved in a physiologically acceptable solvent therefore, which has not been reconstituted from a lyophilizate, which has a pH of from 2.5 to 3.5 and which is preferably contained in a sealed glass container. While the '340 patent discloses injectable, ready-to-use preparations, the '340 patent does not disclose the stabilization of epirubicin hydrochloride itself as a bulk drug.

U.S. Pat. No. 6,376,469 discloses a β-Type form of crystalline amrubicin hydrochloride having improved thermal stability.

It is desirable to have a crystalline form of epirubicin hydrochloride which has improved thermal stability characteristics. Variation of thermal stability for different crystalline forms of epirubicin hydrochloride is described for the first time herein.

SUMMARY OF THE INVENTION

The present invention relates to a novel, strictly defined, crystalline form of epirubicin hydrochloride, named herein as "type II" crystalline epirubicin hydrochloride, that has excellent thermal stability. Variation of thermal stability for different crystalline forms of epirubicin hydrochloride is described herein.

Type II crystalline epirubicin hydrochloride is characterized by having a powder X-ray diffraction pattern having average values of diffraction angle (2θ) and relative intensity P(%) as presented in the following table:

| Diffraction Angle 2Θ | Relative Intensity P (%) |
|---|---|
| 5.236 | 9.8 |
| 9.212 | 12.5 |
| 13.732 | 15.5 |
| 16.446 | 4.8 |
| 18.234 | 5 |
| 21.114 | 9.7 |
| 22.529 | 25.5 |
| 24.071 | 29.9 |
| 25.879 | 18.4 |
| 27.762 | 16.5 |
| 29.757 | 10.1 |
| 34.392 | 4.4 |
| 38.157 | 13.1 |
| 44.293 | 5.9 |
| 64.699 | 7.7 |
| 77.815 | 100 |

Accordingly, several objects of the present invention are as follows:

(1) Provide a crystalline form (as well as method of making the same) of epirubicin hydrochloride which is distinguished by improved thermal stability characteristics.

(2) Provide an extraction method in which epirubicin hydrochloride is crystallized from the aqueous portion of an organo-aqueous solution.

(3) Provide an extraction method in which crystallization is conducted within the range of 2 to 5 pH.

(4) Provide an extraction method in which crystallization is conducted at temperatures of 20° C. and above.

(5) Provide an extraction method in which crystallization is conducted with hydrophilic organic solvents such as alcohols, ketone, nitrites, and their mixtures with branched chains of $C_1$-$C_4$.

It thus is an object of the invention to provide a crystalline form (i.e., type II) of epirubicin hydrochloride which is distinguished by other crystalline forms of epirubicin hydrochloride by improved thermal stability characteristics. It is a further object of the invention to provide a method of synthesis for the aforementioned type II crystalline form of epirubicin hydrochloride.

BRIEF DESCRIPTION OF THE DRAWINGS

FIG. 1 illustrates a graph of the temperature vs. heat flow for type II crystalline epirubicin hydrochloride.

FIG. 2 illustrates an IR-spectrum plot of type II crystalline epirubicin hydrochloride.

FIG. 3 illustrates a graph of the temperature vs. heat flow for type I crystalline hydrochloride.

FIG. 4 illustrates an IR-spectrum plot of type I crystalline epirubicin hydrochloride.

FIG. 5 illustrates the powder x-ray diffraction spectrum of type II crystalline epirubicin hydrochloride.

FIG. 6 illustrates the powder x-ray diffraction spectrum of type I crystalline epirubicin hydrochloride.

FIG. 7 illustrates the powder x-ray diffraction spectrum of type I and II crystalline epirubicin hydrochloride.

DETAILED DESCRIPTION OF THE INVENTION

The present invention is directed to type II crystalline epirubicin hydrochloride which can be produced by crystallizing epirubicin hydrochloride from a suitable solvent such as, for example, water or mixture of water and a hydrophilic organic solvent. Preferably, crystallization of type II epirubicin hydrochloride is performed at a temperature of 20° C. or above.

Crystallization is conducted by adding a hydrophilic organic solvent, preferably an alcohol with branched carbon chain $C_1$-$C_3$ to a solution of epirubicin hydrochloride in water or solvent-aqueous mixture. Preferably, the concentration by mass of epirubicin hydrochloride in aqueous or solvent-aqueous solution is from 5% to 50%, and more preferably from 10% to 30%. The pH of the solution is preferably maintained between 2 and 5.

Volume of the solvent preferably exceeds the volume of the epirubicin hydrochloride solution from 2 to 20 times. The crystallization process is conducted at temperatures from 20° C. to 90° C., preferably from 20° C. to 50° C. Time of crystallization varies from between 0.5 to 12 hours, and more preferably between 2 to 5 hours.

Type II crystalline epirubicin hydrochloride obtained by this method is extracted by standard procedures known to those of ordinary skill in the art (e.g., vacuum-filtration through the glass filter or centrifugal filtration) followed by drying of the crystals. The produced type II crystalline epirubicin hydrochloride can be used for preparation of the final dosage forms of epirubicin hydrochloride. By way of illustration and not limitation, the type II crystalline epirubicin hydrochloride can be lyophilized (e.g. freeze dried) or dissolved in solution for intravenous injection. For intravenous injection applications, the type II crystalline epirubicin hydrochloride can be dissolved in a suitable carrier or carriers known to those skilled in the art.

The following two examples disclose methods of producing type II crystalline epirubicin hydrochloride.

EXAMPLE 1

(1) A solution of epirubicin hydrochloride (10.0 grams) in water or in ethanol-in-water mixture (pH 3-4) undergoes low-pressure evaporation at a temperature of 40° C. until a gel state of the solution is achieved.

(2) 1-propanol in the amount of 12-times the volume of the residual solution is then added to the residual solution and stirred for 3 hours.

(3) Precipitated crystals of epirubicin hydrochloride are then collected by filtration, washed in 10 ml of acetone and dried at room temperature.

(4) The result is 9.3 grams of type II epirubicin hydrochloride crystals.

(5) As seen in FIG. 1, the melting point of type II crystalline epirubicin hydrochloride is approximately 207° C. with decomposition (hot stage 2° C./min). FIG. 2 illustrates the IR-spectrum (IR (KBr)) of type II crystalline epirubicin hydrochloride. Peaks/valleys are seen at 3415, 2928, 1720, 1620, 1576, 1510, 1413, 1371, 1284, 1239, 1210, 1162, 1115, 1068, 1019, 991, 930, 908, 880, 814, 768, 719, 693, 595 cm$^{-1}$.

EXAMPLE 2

(1) A solution of epirubicin hydrochloride (10.0 grams) in water or in ethanol-in-water mixture (pH 3-4) undergoes low-pressure evaporation at a temperature of 40° C. until a gel state of the solution is achieved.

(2) Absolute ethanol in the amount of 10-times the volume of the original solution is then added to the residual solution and stirred for 2 hours.

(3) Precipitated crystals of epirubicin hydrochloride are then collected by filtration, washed in 10 ml of ethanol and 10 ml of acetone and dried at room temperature.

(4) The result is 7.5 grams of type II epirubicin hydrochloride crystals.

The following example (Example 3) discloses a method of producing type I epirubicin hydrochloride crystals, namely epirubicin hydrochloride crystals as described in U.S. Pat. No. 4,861,870.

EXAMPLE 3

(1) Step is identical to step 1 in Example 1 above.

(2) Gel solution of epirubicin hydrochloride is poured into 300 ml of acetone.

(3) Precipitated crystals of epirubicin hydrochloride are then collected by filtration and washed in 50 ml of acetone.

(4) The result is 9.7 grams of type I epirubicin hydrochloride crystals.

As seen in FIG. 3, the melting point of type I crystalline epirubicin hydrochloride is approximately 196° C. with decomposition (hot stage 2° C./min). FIG. 4 illustrates the IR-spectrum (IR (KBr)) of type I crystalline epirubicin hydrochloride. Peaks/valleys are seen at 3430, 2934, 2027, 1724, 1617, 1583, 1508, 1445, 1412, 1284, 1236, 1211, 1162, 1121, 1064, 1018, 992, 931, 909, 876, 814, 792, 767, 738, 721, 693, 588, and 465 cm$^{-1}$.

EXAMPLE 4

Optical Microscopy was performed on type I and II crystalline epirubicin hydrochloride as described below:

Microscope used: Labomed CXRIII optical microscope with polarizing filters. The samples of epirubicin hydrochloride obtained in Example 1 (type II) and Reference Example 3 (type I) both exhibit birefringence and are, therefore, anisotropic crystals.

EXAMPLE 5

In this example, powder X-ray diffraction spectra of crystalline epirubicin hydrochloride of type I and type II were obtained. Powder X-ray diffraction spectra were measured using a Rigaku Cu Anode X-ray Diffractometer (MiniFlex). The conditions for analysis of the samples was as follows:

Start angle: 3
Stop angle: 90
Sampling: 0.02
Scan speed: 1.00
X-ray powder diffraction performed with Copper Kα (λ=1.5406 Å incident X-ray)
Vertical θ: 2θ Bertrano Parafocusing Diffractometer
Nil scintillating (Pulse height PMT) detector
Kβ Nickel filter The results of the measured powder X-ray diffraction spectra are as follows:

The X-ray diffraction patterns are dissimilar for the samples obtained in Example 1 (Type II) and Reference Example 3 (Type I). Table 1 shown below illustrates the type II crystalline epirubicin hydrochloride XRD Analysis-Diffraction Angle (2-Θ) versus Relative Intensity (P %). In contrast, Table 2 shown below illustrates the type I crystalline epirubicin hydrochloride XRD Analysis-Diffraction Angle (2-Θ)) versus Relative Intensity (P %).

TABLE 1

Crystalline Epirubicin hydrochloride type II XRD Analysis-Diffraction Angle (2-Θ) versus Relative Intensity (P %).

| 2Θ | d (A) | BG | Peak | P (%) | Area | FWHM |
|---|---|---|---|---|---|---|
| 5.236 | 16.8641 | 22 | 415 | 9.8 | 122 | 0.234 |
| 9.212 | 9.5918 | 15 | 531 | 12.5 | 207 | 0.311 |
| 13.732 | 6.4434 | 40 | 658 | 15.5 | 211 | 0.256 |
| 16.446 | 5.3855 | 122 | 204 | 4.8 | 115 | 0.449 |
| 18.234 | 4.8614 | 74 | 214 | 5 | 105 | 0.39 |
| 21.114 | 4.2042 | 43 | 411 | 9.7 | 233 | 0.453 |
| 22.529 | 3.9433 | 323 | 1084 | 25.5 | 405 | 0.299 |
| 24.071 | 3.6941 | 102 | 1272 | 29.9 | 422 | 0.265 |
| 25.879 | 3.44 | 75 | 780 | 18.4 | 348 | 0.357 |
| 27.762 | 3.2108 | 71 | 701 | 16.5 | 319 | 0.363 |
| 29.757 | 2.9999 | 109 | 428 | 10.1 | 150 | 0.279 |
| 34.392 | 2.6055 | 67 | 186 | 4.4 | 101 | 0.434 |
| 38.157 | 2.3566 | 114 | 558 | 13.1 | 196 | 0.28 |
| 44.293 | 2.0433 | 78 | 249 | 5.9 | 91 | 0.292 |
| 64.699 | 1.4395 | 19 | 328 | 7.7 | 130 | 0.316 |
| 77.815 | 1.2264 | 41 | 4250 | 100 | 1817 | 0.342 |

TABLE 2

Crystalline Epirubicin hydrochloride type I XRD Analysis-Diffraction Angle (2-Θ) versus Relative Intensity (P %).

| 2-Θ | d (A) | BG | Peak | P (%) | Area | FWHM |
|---|---|---|---|---|---|---|
| 38.236 | 2.3519 | 8 | 1750 | 47.7 | 585 | 0.267 |
| 44.453 | 2.0363 | 6 | 802 | 21.9 | 302 | 0.301 |
| 64.825 | 1.4371 | 7 | 373 | 10.2 | 141 | 0.301 |
| 77.955 | 1.2246 | 21 | 3667 | 100 | 1520 | 0.331 |
| 82.139 | 1.1725 | 12 | 277 | 7.6 | 120 | 0.344 |

Type I crystalline epirubicin hydrochloride gives a single strong signal at approximately 38 degrees. In contrast, type II crystalline epirubicin hydrochloride gives multiple strong signals across the entire spectrum. FIG. 5 illustrates the powder X-ray diffraction spectrum of type II crystalline epirubicin hydrochloride obtained in Example 1. FIG. 6 illustrates the powder X-ray diffraction spectrum of type I crystalline epirubicin hydrochloride obtained in Example 3 (Reference). FIG. 7 shows the superimposed X-ray diffraction spectra of type I and type II crystalline epirubicin hydrochloride.

EXAMPLE 6

The following example illustrates the improved thermal stability of type II crystalline epirubicin hydrochloride as compared to type I crystalline epirubicin hydrochloride.

The type II crystalline epirubicin hydrochloride obtained in Example 1 and type 1 crystalline epirubicin hydrochloride obtained in reference Example 3 were each kept at a temperature 40° C. for six months, thereby mimicking accelerated storage conditions. The thermal stability was investigated and measured by studying the following parameters: (1) assay (HPLC method), (2) doxorubicinone quantity (doxorubicinone, an aglycone of epirubicin, is the major epirubicin degradation product), and (3) total impurities. The results of this investigation is presented in Tables 3 and 4 listed below.

Anhydrous and solvent-free basis

TABLE 3

Stability Data for type II crystalline epirubicin hydrochloride.

Accelerated storage conditions 40° C. ± 2° C.

| | Batch ESP01 | | | Batch ESP02 | | | Batch ESP03 | | |
|---|---|---|---|---|---|---|---|---|---|
| Months | Assay* | Doxo-Rubicinone | Total impurities | Assay* | Doxorubicinone | Total impurities | Assay* | Doxorubicinone | Total impurities |
| Initial | 99.2 | 0.04 | 0.39 | 99.3 | Not detected | 0.37 | 99.0 | 0.06 | 0.42 |
| 3 | 99.1 | 0.07 | 0.44 | 99.0 | 0.06 | 0.44 | 99.1 | 0.12 | 0.48 |
| 6 | 99.1 | 0.12 | 0.50 | 99.0 | 0.14 | 0.51 | 99.0 | 0.15 | 0.53 |

*Anhydrous and solvent-free basis

TABLE 4

Stability Data for type I crystalline epirubicin hydrochloride.

Accelerated storage conditions 40° C. ± 2° C.

| | Sample ESP04 | | | Sample ESP05 | | | Sample ESP06 | | |
|---|---|---|---|---|---|---|---|---|---|
| Months | Assay* | Doxorubicinone | Total impurities | Assay* | Doxorubicinone | Total impurities | Assay* | Doxorubicinone | Total impurities |
| Initial | 98.8 | 0.17 | 0.42 | 99.0 | 0.21 | 0.45 | 99.2 | 0.07 | 0.42 |
| 3 | 94.3 | 2.1 | 2.7 | 94.0 | 2.4 | 3.0 | 95.1 | 1.8 | 2.4 |
| 6 | 89.0 | 6.0 | 7.6 | 90.1 | 5.8 | 7.7 | 90.2 | 5.4 | 6.9 |

*Anhydrous and solvent-free basis

As the results in Tables 3 and 4 confirm, type II crystalline epirubicin hydrochloride exhibits much greater thermal stability than type I crystalline epirubicin hydrochloride. This is particularly advantageous because the type II crystalline epirubicin hydrochloride will retain its efficacy for a longer period of time as compared to type I crystalline epirubicin hydrochloride because there is less degradation and impurities. This also means that the shelf life of type II crystalline epirubicin hydrochloride is longer than the shelf life of type I crystalline epirubicin hydrochloride.

While embodiments of the present invention have been shown and described, various modifications may be made without departing from the scope of the present invention. The invention, therefore, should not be limited, except to the following claims, and their equivalents.

We claim:

1. A crystalline epirubicin hydrochloride having a powder X-ray diffraction pattern having average values of diffraction angle (2θ) and relative intensity (P(%)) as presented in the following table:

| Diffraction Angle 2Θ | Relative Intensity P (%) |
|---|---|
| 5.236 | 9.8 |
| 9.212 | 12.5 |
| 13.732 | 15.5 |
| 16.446 | 4.8 |
| 18.234 | 5 |
| 21.114 | 9.7 |
| 22.529 | 25.5 |
| 24.071 | 29.9 |
| 25.879 | 18.4 |
| 27.762 | 16.5 |
| 29.757 | 10.1 |
| 34.392 | 4.4 |
| 38.157 | 13.1 |
| 44.293 | 5.9 |
| 64.699 | 7.7 |
| 77.815 | 100. |

2. A crystalline epirubicin hydrochloride according to claim 1 having a melting point of approximately 207° C.

3. A process of preparing a crystalline epirubicin hydrochloride according to claim 1 comprising:

adding one of (a) a hydrophilic organic solvent or (b) a mixture of hydrophilic organic solvent in water, to a solution of epirubicin hydrochloride; and crystallizing the epirubicin hydrochloride to produce the crystalline epirubicin hydrochloride according to claim 1 at a temperature from 20° C. to 90° C. and at a pH from 3 to 4.

4. A process according to claim 3 wherein said hydrophilic organic solvent comprises one of the following: 1-propanol, ethanol or an alcohol with branched carbon chain $C_1$-$C_3$.

5. A process of preparing a crystalline epirubicin hydrochloride according to claim 1 comprising:

a. dissolving epirubicin hydrochloride in water or in a mixture of hydrophilic organic solvent in water to form a solution;

b. adjusting the pH of the solution to a value from 3 to 4.

c. evaporating the solution at a temperature of about 40° C. until the solution is in a gel state; and d. crystallizing epirubicin hydrochloride by adding a second hydrophilic organic solvent at a temperature from 20° C to 90° C.

6. A process according to the claim 4, wherein the hydrophilic organic solvent comprises 1-propanol or ethanol.

7. A process according to claim 5, wherein the second hydrophilic organic solvent comprises 1-propanol or ethanol.

8. A process according to claim 5, wherein the second hydrophilic organic solvent comprises an alcohol with branched carbon chain $C_1$-$C_3$.

* * * * *